(12) United States Patent
Kurashima et al.

(10) Patent No.: US 9,126,885 B2
(45) Date of Patent: Sep. 8, 2015

(54) METHOD FOR PURIFYING 2,3,3,3-TETRAFLUOROPROPENE

(71) Applicant: ASAHI GLASS COMPANY, LIMITED, Chiyoda-ku (JP)

(72) Inventors: Kazuyoshi Kurashima, Chiyoda-ku (JP); Kunio Watanabe, Chiyoda-ku (JP); Hiroshi Yamamoto, Chiyoda-ku (JP)

(73) Assignee: Asahi Glass Company, Limited, Chiyoda-ku (JP)

( * ) Notice: Subject to any disclaimer, the term of this patent is extended or adjusted under 35 U.S.C. 154(b) by 56 days.

(21) Appl. No.: 13/959,096

(22) Filed: Aug. 5, 2013

(65) Prior Publication Data

US 2013/0317262 A1 Nov. 28, 2013

Related U.S. Application Data

(63) Continuation of application No. PCT/JP2012/052545, filed on Feb. 3, 2012.

(30) Foreign Application Priority Data

Feb. 4, 2011 (JP) .................................. 2011-022871

(51) Int. Cl.
C07C 17/38 (2006.01)
C07C 21/18 (2006.01)

(52) U.S. Cl.
CPC .................................... C07C 17/38 (2013.01)

(58) Field of Classification Search
CPC ....................................................... C07C 17/38
USPC .......................... 570/262, 263, 238, 180, 216
See application file for complete search history.

(56) References Cited

U.S. PATENT DOCUMENTS

2010/0193347 A1 8/2010 Hulse et al.

FOREIGN PATENT DOCUMENTS

| JP | 56-166128 | 12/1981 |
| JP | 9-255597 | 9/1997 |
| JP | 2010-37343 | 2/2010 |
| JP | 2010-509333 | 3/2010 |
| JP | 2010-202640 | 9/2010 |
| JP | 2012-1495 | 1/2012 |
| WO | 2008/060614 | 5/2008 |

OTHER PUBLICATIONS

International Search Report issued May 15, 2012 in PCT/JP2012/052545 filed Feb. 3, 2012.

*Primary Examiner* — Jafar Parsa
*Assistant Examiner* — Medhanit Bahta
(74) *Attorney, Agent, or Firm* — Oblon, McClelland, Maier & Neustadt, L.L.P.

(57) ABSTRACT

To provide a method for purifying R-1234yf, whereby it is possible to efficiently remove even impurities such as R-1243zf, etc. which are difficult to separate by distillation purification, from a mixture containing R-1234yf as the main component and various impurities, such as a gas formed by reacting R-1214ya with hydrogen. The method for purifying R-1234yf comprises a step of bringing a mixture which contains R-1234yf as the main component and also contains hydrohaloalkene impurities other than R-1234yf and hydrohaloalkane impurities, into contact with a solvent that has an extraction/removal index (r), as represented by the formula $r=[4\times(\delta D-17.2)^2+(\delta P-8.3)^2+(\delta H-2.6)^2]^{1/2}$, of at most 6.5, so as to remove at least a part of the hydrohaloalkene impurities and hydrohaloalkane impurities.

10 Claims, 1 Drawing Sheet

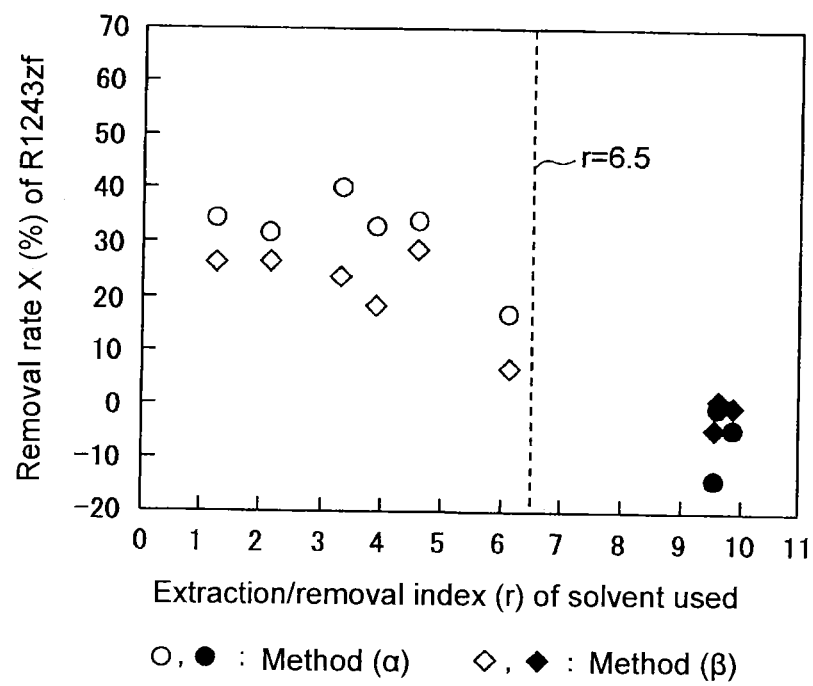

METHOD FOR PURIFYING 2,3,3,3-TETRAFLUOROPROPENE

TECHNICAL FIELD

The present invention relates to a method for purifying 2,3,3,3-tetrafluoropropene.

BACKGROUND ART 2,3,3,3-tetrafluoropropene ($CF_3CF=CH_2$, R-1234yf) contains no chlorine and therefore is useful as a substitute compound for flons such as chlrofluorocarbons to be used as e.g. refrigerants.

A method for producing R-1234yf may, for example, be a method of reacting and reducing 1,1-dichloro-2,3,3,3-tetrafluoropropene ($CF_3CF=CCl_2$, R-1214ya) with hydrogen to obtain R-1234yf (e.g. Patent Document 1).

However, a gas formed by reacting and reducing R-1214ya with hydrogen, contains, in addition to R-1234yf, hydrohaloalkene impurities such as 3,3,3-trifluoropropene ($CF_3CH=CH_2$, R-1243zf) and hydrohaloalkane impurities such as 1,1,1,2-tetrafluoropropane ($CF_3CHFCH_3$, R-254eb). As a method for purifying R-1234yf from such a formed gas, a method is widely used in which the formed gas is liquefied and then subjected to distillation purification. However, among the above-mentioned impurities, those resembling R-1234yf in their structures have boiling points close to the boiling point of R-1234yf, and thus it is difficult to separate them by distillation purification. Especially, R-1243zf has a boiling point of −22° C. which is very close to the boiling point of −29° C. of R-1234yf, and thus it is very difficult to separate it by distillation purification.

PRIOR ART DOCUMENT

Patent Document

Patent Document 1: WO 2008/060614

DISCLOSURE OF INVENTION

Technical Problem

It is an object of the present invention to provide a method for purifying R-1234yf, whereby it is possible to effectively remove even impurities such as R-1243zf, etc. which are difficult to separate by distillation purification, from a mixture containing R-1234yf as the main component and various impurities, such as a gas formed by reacting R-1214ya with hydrogen.

Solution to Problem

The present invention has adopted the following constructions to solve the above-mentioned problem.
[1] A method for purifying R-1234yf comprising a step of bringing a mixture which contains 2,3,3,3-tetrafluoropropene as the main component and also contains hydrohaloalkene impurities other than 2,3,3,3-tetrafluoropropene and hydrohaloalkane impurities, into contact with a solvent that has an extraction/removal index (r), as represented by the following formula (1), of at most 6.5, so as to remove at least a part of the hydrohaloalkene impurities and hydrohaloalkane impurities:

$$r=[4\times(\delta D-17.2)^2+(\delta P-8.3)^2+(\delta H-2.6)^2]^{1/2} \quad (1)$$

wherein δD, δP and δH are, respectively, dispersion parameter, polar parameter and hydrogen bonding parameter in the Hansen solubility parameters of the solvent, the unit of each of which is $(MPa)^{1/2}$.
[2] The method for purifying R-1234yf according to [1], wherein the hydrohaloalkene impurities include a hydrohalopropene.
[3] The method for purifying R-1234yf according to [1] or [2], wherein the hydrohaloalkane impurities include at least one of a hydrohalopropane and a hydrohaloethane.
[4] The method for purifying R-1234yf according to any one of [1] to [3], wherein at least a part of at least one member selected from the group consisting of 3,3,3-trifluoropropene, 3,3-difluoropropene and 1,2,3,3,3-pentafluoropropene, as the hydrohaloalkene impurities, is removed from the mixture.
[5] The method for purifying R-1234yf according to any one of [1] to [3], wherein at least a part of 3,3,3-trifluoropropene, as the hydrohaloalkene impurities, is removed from the mixture.
[6] The method for purifying R-1234yf according to any one of [1] to [5], wherein at least a part of at least one member selected from the group consisting of 1,1,1,2-tetrafluoropropane, 1,1,1-triifluoropropane and 1-chloro-1,2,2,2-tetrafluoroethane, as the hydrohaloalkane impurities, is removed from the mixture.
[7] The method for purifying R-1234yf according to any one of [1] to [6], wherein the mixture to be brought into contact with the solvent, is gaseous.

Advantageous Effects of Invention

According to the method for purifying R-1234yf of the present invention, it is possible to effectively remove even impurities such as R-1243zf, etc. which are difficult to separate by distillation purification, from a mixture containing R-1234yf as the main component and various impurities, such as a gas formed by reacting R-1214ya with hydrogen.

BRIEF DESCRIPTION OF DRAWING

FIG. 1 is a graph showing a relation between the extraction/removal index (r) of a solvent and the removal rate of R-1243zf in Examples of the present invention and Comparative Examples.

DESCRIPTION OF EMBODIMENTS

The method for purifying 2,3,3,3-tetrafluoropropene (R-1234yf) of the present invention is a method comprising a step of bringing a mixture which contains R-1234yf as the main component and also contains hydrohaloalkene impurities other than R-1234yf (hereinafter referred to simply as "hydrohaloalkene impurities") and hydrohaloalkane impurities, into contact with a solvent (hereinafter referred to as "solvent (A)") that has an extraction/removal index (r) of at most 6.5, as described hereinafter, so as to remove at least a part of the hydrohaloalkene impurities and hydrohaloalkane impurities. Hereinafter, the hydrohaloalkene impurities and hydrohaloalkane impurities may, as they are put together, be referred to simply as "impurities".

In the method for purifying R-1234yf of the present invention, a solvent (A) is used which has an extraction/removal index (r), as represented by the following formula (1), of at most 6.5.

$$r=[4\times(\delta D-17.2)^2+(\delta P-8.3)^2+(\delta H-2.6)^2]^{1/2} \quad (1)$$

wherein δD, δP and δH are, respectively, dispersion parameter, polar parameter and hydrogen bonding parameter in the Hansen solubility parameters (hereinafter referred to as "HSP") of the solvent, the unit of each of which is $(MPa)^{1/2}$.

In the present invention, the method comprises a step of bringing the mixture into contact with the solvent (A) showing a specific solubility to impurities such as R-1243zf such that the extraction/removal index (r) is at most 6.5, whereby the impurities in the mixture are extracted, separated and removed into the solvent (A). The above formula (1) is a formula drawn based on the formula: $(Ra)^2=4\times(\delta D_2-\delta D_1)^2+(\delta P_2-\delta P_1)^2+(\delta H_2-\delta H_1)^2$ which is well known as a formula to obtain the distance Ra between two points in three-dimensional space of HSP.

HSP are ones having the solubility parameter introduced by Hildebrand divided into three components of dispersion parameter δD, polar parameter δP and hydrogen bonding parameter δH and represented in three-dimensional space. Dispersion parameter δD represents the effects by dispersion forces, polar parameter δP represents the effects by dipolar intermolecular forces, and hydrogen bonding parameter δH represents the effects by hydrogen bonding forces.

The definitions and calculations of HSP are disclosed in the following literature.

Edited by Charles M. Hansen, Hansen Solubility Parameters: A Users Handbook (CRC press, 2007)

HSP [δD, δP and δH] of a solvent can simply be estimated form its chemical structure by using e.g. a computer software Hansen Solubility Parameters in Practice (HSPiP). In the present invention, with respect to solvents registered in the data base of HSPiP version 3. 0. 38, the registered values will be used, and with respect to solvents not registered in the data base, values to be estimated by HSPiP version 3. 0. 38 will be used.

Now, the above formula (1) and the method for drawing the condition that the extraction/removal index (r) is at most 6.5, will be described. The extraction/removal index (r) as drawn in the present invention, is drawn by a method comprising the following steps (x) and (y), based on the formula: $(Ra)^2=4\times(\delta D_2-\delta D_1)^2+(\delta P_2-\delta P_1)^2+(\delta H_2-\delta H_1)^2$.

(x) A mixture containing R-1234yf as the main component and optional impurities, is brought in contact under specific conditions with each of a plurality of solvents, of which HSP [δD, δD and δH] are known, whereby a removal rate X (unit: %) of impurity a to be removed among the optional impurities in the mixture, is calculated.

(y) By finding such a sphere that all coordinates of HSP of solvents, of which the removal rates X are at least a certain specific value, are included inside of the sphere and all coordinates of HSP of solvents, of which the removal rates X are less than the specific value, are outside of the sphere, from the center coordinates [δD$_0$, δP$_0$ and δH$_0$] of the sphere, the formula: $r=[4\times(\delta D-\delta D_0)^2+(\delta P-\delta P_0)^2+(\delta H-\delta H_0)^2]^{1/2}$ is drawn, and the radius of the sphere is taken as the maximum value of the extraction/removal index (r).

In step (x), the removal rate (X) (unit: %) of impurity a to be removed, is calculated by the following formula:

$$X=[Y-Z]/Y\times 100 \quad (2)$$

wherein Y is the concentration of impurity a to be removed in the mixture before the contact with the solvent (A), and Z is the concentration of the impurity a in the mixture after the contact with the solvent (A).

The concentration of impurity a can be measured by e.g. gas chromatography.

The method for finding the sphere in step (y) may, for example, be a method of using the Sphere function of HSPiP.

Specifically, in the present invention, the formula (1) and the extraction/removal index (r) were obtained by taking, as the impurity a to be removed, R-1243zf which is close in its boiling point to R-1234yf and is difficult to remove by distillation purification, among the hydrohaloalkene impurities and hydrohaloalkane impurities contained in the mixture. And, in step (y), by finding such a sphere that all coordinates of HSP of solvents, of which removal rates (X) are at least 5%, are included inside of the sphere, the coordinates [17.2, 8.3, 2.6] of the sphere and the maximum value 6.5 of the extraction/removal index (r) were obtained.

As the solvent (A), solvents listed in Tables 1 and 2 may, for example, be mentioned.

TABLE 1

| Solvent | Extraction/removal index (r) |
|---|---|
| 1,1-dichloroethane | 1.5 |
| 1,1,1-trichloroethane | 4.1 |
| 1,2-dichloropropane | 1.3 |
| 3-chloro-1-propene | 2.2 |
| 2-chloro-2-methylpropane | 3.3 |
| 2-chloro-2-methyl-1-propene | 3.4 |
| 1-chlorobutane | 3.5 |
| 2-bromobutane | 2.6 |
| 4-bromo-1-butene | 3.3 |
| Chlorocyclohexane | 2.9 |
| Methyltrichlorosilane | 2.4 |
| 1,1-dichloroacetone | 2.9 |
| Diethyl ketone | 3.6 |
| 3-methylcyclohexanone | 2.4 |
| 3-heptanone | 4.1 |
| Isophorone | 2.5 |
| Carvone | 3.3 |
| 2,3-butanedione | 6.1 |
| Trichloroacetonitrile | 4.0 |
| Decyl aldehyde | 3.6 |
| Hexyl formate | 5.6 |
| Isobornyl acetate | 5.0 |
| Menthyl acetate | 3.3 |
| Ethyl phenylacetate | 5.3 |
| Butyl propionate | 5.3 |
| Diisodecyl phthalate | 2.1 |
| γ-dodecalactone | 2.4 |

TABLE 2

| Solvent | Extraction/removal index (r) |
|---|---|
| Dibutyl sebacate | 4.2 |
| Butyl mercaptan | 4.0 |
| Tetrahydrofuran | 5.7 |
| 2-methyltetrahydrofuran | 3.8 |
| Dihydropyran | 4.2 |
| Tetrahydropyran | 4.3 |
| Methoxycyclopentane | 5.5 |
| 2-chloroethyl ethyl ether | 2.7 |
| Anisole | 5.9 |
| 4-methoxytoluene | 5.2 |
| Ethylal | 5.5 |
| 1,3-dimethoxybutane | 5.0 |
| Ethylene glycol butyl methyl ether | 5.1 |
| Ethylene glycol dibutyl ether | 5.1 |
| 2-methoxytetrahydropyran | 3.8 |
| 2-methyl-1,3-dioxolane | 4.7 |
| Paraldehyde | 5.3 |
| Diethylene glycol diethyl ether | 5.4 |
| Diethylene glycol dibutyl ether | 4.9 |
| 1,8-cineole | 3.9 |
| Menthofuran | 4.8 |
| N-ethyl morpholine | 5.3 |

TABLE 2-continued

| Solvent | Extraction/removal index (r) |
|---|---|
| Dibutyl sulfide | 5.6 |
| Ethylhexylamine | 6.2 |
| Piperazine | 4.9 |
| Butyl quinoline | 4.9 |
| Xylene | 4.6 |

As the solvent (A), one of such solvents may be used alone, or two or more of them may be used in combination.

As the solvent (A), a solvent having an extraction/removal index (r) of at most 6.5 is preferred, and a solvent having an extraction/removal index (r) of at most 5.0 is more preferred, since the efficiency for removal of R-1243zf thereby tends to be particularly high.

The boiling point of the solvent (A) is preferably at least 40° C., more preferably at least 90° C., from the viewpoint of the efficiency for removal of impurities.

The solvent (A) is preferably anisole, 4-bromo-1-butene, 2-bromobutane, butyl propionate, butyl mercaptan, 3-chloro-1-propene, 2-chloro-2-methylpropane, 1-chlorobutane, decyl aldehyde, dibutyl sebacate, dibutyl sulfide, 1,1-dichloroethane, 1,2-dichloropropane, diethyl ketone, diethylene glycol dibutyl ether, diethylene glycol dimethyl ether, diisodecyl phthalate, ethylhexylamine, 3-heptanone, hexyl formate, isophorone, methyltrichlorosilane, 2-methyltetrahydrofuran, paraldehyde, piperazine, tetrahydrofuran, 1,1,1-trichloroethane, 2,3-butanedione, 2-chloroethyl ethyl ether, 1,8-cineole, chlorocyclohexane, 1,1-dichloroacetone, dihydropyran, 1,3-dimethoxybutane, N-ethyl morpholine, ethylene glycol butylmethyl ether, ethylene glycol dibutyl ether, menthofuran, menthyl acetate, 2-methoxytetrahydropyran, 3-methylcyclohexanone, 2-methyl-1,3-dioxolane, tetrahydropyran, trichloroacetonitrile, ethyl phenyl acetate, 4-methoxytoluene, ethylal, carvone, γ-dodecalactone, isobornyl acetate, butyl quinoline, methoxycyclopentane or xylene, more preferably, anisole, 2-bromobutane, butyl propionate, 2-chloro-2-methylpropane, 1,1-dichloroethane, 1,2-dichloropropane, diethyl ketone, diethylene glycol dimethyl ether, ethylhexylamine, hexyl formate, isophorone, paraldehyde, tetrahydrofuran, 2,3-butanedione, 1,1-dichloroacetone, menthofuran, 2-methoxytetrahydropyran, 3-methylcyclohexanone, 2-methyl-1,3-dioxolane, tetrahydropyran, trichloroacetonitrile, ethyl phenyl acetate, 4-methoxytoluene, ethylal, carvone, γ-dodecalactone, isobornyl acetate or xylene, particularly preferably, 2-bromobutane, 2-chloro-2-methylpropane, 1,1-dichloroethane, 1,2-dichloropropane, diethyl ketone, 1,1-dichloroacetone, 3-methylcyclohexanone, trichloroacetonitrile, γ-dodecalactone or xylene.

In the method for purifying R-1234yf of the present invention, it is preferred to remove at least 5%, more preferred to remove at least 10%, of the hydrohaloalkene impurities and hydrohaloalkane impurities.

Further, in the method for purifying R-1234yf of the present invention, it is preferred to remove at least 5%, more preferred to remove at least 10%, of at least one member selected from the group consisting of 3,3,3-trifluoropropene, 3,3-difluoropropene and 1,2,3,3,3-pentafluoropropene as the hydrohaloalkene impurities, from a mixture containing hydrohaloalkene impurities other than 2,3,3,3-tetrafluoropropene and hydrohaloalkane impurities.

Still further, in the method for purifying R-1234yf of the present invention, it is preferred to remove at least 5%, more preferred to remove at least 10%, of 3,3,3-trifluoropropene as hydrohaloalkene impurities, from the mixture.

Still further, in the method for purifying R-1234yf of the present invention, it is preferred to remove at least 5%, more preferred to remove at least 10%, of at least one member selected from the group consisting of 1,1,1,2-tetrafluoropropane, 1,1,1-trifluoropropane and 1-chloro-1,2,2,2-tetrafluoroethane as the hydrohaloalkane impurities, from the mixture.

As the method for bringing the mixture into contact with the solvent (A), the following method (α) or (β) may, for example, be mentioned depending on the difference in the state of the mixture to be brought into contact with the solvent (A).

(α) A method of bringing a gaseous mixture (hereinafter referred to as "mixed gas") into contact with the solvent (A).

(β) A method of bringing a liquid mixture (hereinafter referred to as "mixed liquid") into contact with the solvent (A).

(Method (α))

The method (α) may, for example, be a method of blowing the mixed gas into the solvent (A) and recovering a purified gas passed through the solvent (A).

In the method (α), the purification may be a batch system or a continuous system.

In the method (α), the temperature of the solvent (A) may be at any level so long as it is at least the melting point and at most the boiling point of the solvent (A), and it is preferably from −30 to 70° C., more preferably from −30 to 40° C. When the temperature of the solvent (A) is at least the lower limit value, the energy required for cooling may be low, and the installation, etc. may be simple. When the temperature of the solvent (A) is at most the upper limit value, the impurities in the mixed gas tend to be readily dissolved and extracted in the solvent (A), whereby the efficiency for removal of the impurities will be improved.

In the method (α), the pressure (the absolute pressure) during the purification may be at most the liquefaction pressure of R-1234yf, preferably from 10 to 600 kPa, more preferably from 100 to 300 kPa. When the pressure is at least the lower limit value, the efficiency for removal of the impurities will be improved, and when the pressure is at most the upper limit value, the handling efficiency will be good, and the installation, etc. may be simple.

In the method (α), the blowing flow rate of the mixed gas per 200 mL (milliliters) of the solvent (A) is preferably from 2 to 50 mL/min., more preferably from 10 to 20 mL/min. When the blowing flow rate of the mixed gas is at least the lower limit value, the amount of R-1234yf obtainable by the purification increases. When the blowing flow rate of the mixed gas is at most the upper limit value, the efficiency for removal of the impurities will be improved. The contact time is preferably at least 0.5 second, more preferably at least 1 second. When the contact time is long, the efficiency for removal of the impurities will be improved.

In the method (α), the total amount of the impurities contained in the mixed gas is preferably at most 10 mass %, more preferably at most 2 mass %, to the total mass of the solvent (A) from the viewpoint of the efficiency for removal of the impurities. That is, in the method (α), it is preferred to carry out the purification by adjusting the total blowing flow rate of the mixed gas into the solvent (A) so that the proportion of the impurities to the solvent (A) would be at most the above upper limit value.

The reactor to be used for the method (α) is not particularly limited so long as it is capable of accommodating the solvent (A) to bring the mixed gas into contact therewith and recovering a purified gas after the contact, and a known reactor may be employed.

The material for the reactor may, for example, be glass, iron, nickel or an alloy containing such metal as the main component, or a fluorinated resin such as a tetrafluoroethylene/perfluoro(alkyl vinyl ether) copolymer (PFA).

(Method (β))

The method (β) may, for example, be a method of adding the mixed liquid to a container containing the solvent (A) and recovering a purified gas obtained in a gas phase portion of the container through the solvent (A).

In the method (β), the purification may be a batch system or a continuous system.

In the method (β), the temperature of the solvent (A) is at least the melting point and at most the boiling point of the solvent (A). The temperature of the solvent (A) is preferably from −30 to 70° C., more preferably from −30 to 40° C. When the temperature of the solvent (A) is at least the lower limit value, the energy required for cooling may be low, and the installation, etc. may also be simple. When the temperature of the solvent (A) is at most the upper limit value, the efficiency for removal of the impurities will be improved.

In the method (β), the pressure (gauge pressure) in the container is preferably from −91 to 2,000 kPaG, more preferably from 0 to 200 kPaG. When the pressure is at least the lower limit value, the efficiency for removal of the impurities will be improved. When the pressure is at most the upper limit value, the handling efficiency will be good, and the installation, etc. may be simple.

In the method (β), the total amount of the impurities contained in the mixed liquid is preferably at most 10 mass %, more preferably at most 2 mass %, to the total amount of the solvent (A) from the viewpoint of the efficiency for removal of the impurities. That is, in the method (β), it is preferred to carry out the purification by adjusting the total amount of the mixed liquid to be in contact with the solvent (A) so that the proportion of the impurities to the solvent (A) would be at most the above upper limit value. The residence time is preferably at least 30 minutes, more preferably at least one hour. When the residence time is long, the efficiency for removal of the impurities will be improved.

The reactor to be used for the method (β) may be any reactor so long as it is capable of bringing the mixed liquid into contact the solvent (A) and then recovering a purified gas obtainable in a gas phase, and a known reactor may be employed.

The material for the reactor may, for example, be glass, iron, nickel or an alloy containing such metal as the main component, or a fluorinated resin such as a tetrafluoroethylene/perfluoro(alkyl vinyl ether) copolymer (PFA).

In the step of bringing the mixture into contact with the solvent (A) to remove impurities, it is preferred to employ the method (α) rather than the method (β), since the efficiency for removal of impurities is thereby higher. Further, from such a viewpoint that the installation becomes simple, it is advantageous to employ the method (α) when the mixture to be purified is obtained in a gaseous state, or to employ the method (β) when the mixture is obtained in a liquid state.

The purification method of the present invention may have another step of removing impurities which cannot be removed in the step of bringing the mixture into contact with the solvent (A), as the case requires. Such another step may, for example, be a step of removing impurities by a known distillation purification. Such another step may be carried out before or after the above-described step of bringing the mixture into contact with the solvent (A) to remove impurities.

The mixture to be purified by the purification method of the present invention contains R-1234yf as the main component. "The mixture contains R-1234yf as the main component" means that the content of R-1234yf in the mixture is at least 50 vol %. The content of R-1234yf in the mixture is preferably at least 70 vol %, more preferably at least 75 vol %, whereby highly pure R-1234yf is readily obtainable. Further, the upper limit for the content of R-1234yf in the mixture is not particularly limited, but is practically about 90 vol %.

Further, the mixture contains hydrohaloalkene impurities and hydrohaloalkane impurities. A hydrohaloalkene is an alkene other than R-1234yf, which has both hydrogen atoms and halogen atoms. Likewise, a hydrohaloalkane is an alkane which has both hydrogen atoms and halogen atoms. The halogen atoms may, for example, be chlorine atoms, fluorine atoms, etc.

The hydrohaloalkene impurities in the mixture may be of one type or of two or more types.

The purification method of the present invention is effective for removing hydrohalopropenes close to R-1234yf in their boiling points, as the hydrohaloalkene impurities. Specifically, it is effective for removing at least one member selected from the group consisting of R-1243zf, 1,2,3,3,3-pentafluoropropene ($CF_3CF=CHF$, R-1225ye, boiling point: −19° C.) and 3,3-difluoropropene ($CHF_2CH=CH_2$, R-1252zf, boiling point: −27° C.). Among them, the purification method of the present invention is particularly effective for removing R-1243zf as the hydrohaloalkene impurities, since it is capable of highly efficiently removing even R-1243zf which is very close to R-1234yf in the boiling point and is therefore difficult to separate by distillation purification.

The hydrohaloalkane impurities in the mixture may be of one type or of two or more types.

The purification method of the present invention is effective for removing at least one of a hydrohalopropane and a hydrohaloethane, as the hydrohaloalkane impurities. The hydrohalopropane may, for example, be 1,1,1,2-tetrafluoropropane ($CF_3CHFCH_3$, R-254eb, boiling point: −6° C.) or 1,1,1-trifluoropropane ($CF_3CH_2CH_3$, R-263fb, boiling point: −13° C.). The hydrohaloethane may, for example, be 1-chloro-1,2,2,2-tetrafluoroethane ($CF_3CHClF$, R-124, boiling point: −12° C.). The purification method of the present invention is effective for removing at least one member selected from the group consisting of R-254eb, R-263fb and R-124, as the hydrohaloalkane impurities.

The mixture which contains R-1234yf as the main component and contains the hydrohaloalkene impurities and the hydrohaloalkane impurities, may, for example, be a product obtainable by reacting and reducing R-1214ya with hydrogen in the presence of a catalyst. If impurities such as R-1243zf, etc. which are close to R-1234yf in their boiling points, are contained in the desired R-1234yf such as the product obtained by hydrogen reduction of R-1214ya, it is difficult to remove such impurities by distillation purification. Further, in a case where impurities are to be extracted and removed with a solvent, it is common to select a solvent having a high solubility for the impurities. However, if the desired product and the impurities are equivalent in the solubility in the solvent, it is difficult to thereby separate them. For example, HSP of R-1243zf are [14.4, 4.4, 2.7] which are close to HSP[14.2, 3.9, 1.6] of R-1234yf, and accordingly, a solvent exhibiting a high solubility of R-1243zf also exhibits a high solubility of R-1234yf.

Whereas, according to the purification method of the present invention, by using an extraction/removal index (r) represented by the formula (1), it is readily possible to find out a specific solvent (A) which presents a sufficient difference for removal of impurities between the solubility of impurities such as R-1243zf, etc. and the solubility of R-1234yf, and by using such a solvent (A), it is possible to efficiently remove even impurities such as R-1243zf, etc. which are difficult to separate by distillation purification.

EXAMPLES

Now, the present invention will be described in detail with reference to Examples, but it should be understood that the present invention is by no means restricted by such description. Examples 1 to 6 and 10 to 15 are working examples of the present invention and Examples 7 to 9 and 16 to 18 are comparative examples.

[Gas Composition and Removal Rate X]

The compositions of purified gases and mixed gases used in Examples were measured by gas chromatography. Further, the removal rate X (%) of each impurity was calculated by the following formula:

$$X = [Y-Z]/Y \times 100$$

wherein Y is the concentration of the impurity in a mixed gas before the purification, and Z is the concentration of the impurity in a purified gas.

Method (α)

Example 1

Into a three-necked flask equipped with an Allihn condenser and a magnetic stirrer, 155.5 g of 2-chloro-2-methylpropane (extraction/removal index (r)=3.3, temperature: 20° C.) was charged as a solvent (A). With stirring, 9.9 g of a mixed gas containing R-1234yf as the main component and having a composition as shown in Table 3, was bubbled at a flow rate of 12.9 mL/min, and a purified gas passed through the condenser was recovered. The composition of the obtained purified gas and the removal rate X of each impurity are shown in Table 3.

Examples 2 to 9

A purified gas was recovered in the same manner as in Example 1 except that the type and amount of the solvent used, and the composition, gas flow rate and gas flow amount of the mixed gas, were changed as shown in Table 3. The composition of the obtained purified gas and the removal rate X of each impurity are shown in Table 3.

TABLE 3

|  |  | Ex. 1 | Ex. 2 | Ex. 3 | Ex. 4 | Ex. 5 | Ex. 6 | Ex. 7 | Ex. 8 | Ex. 9 |
| --- | --- | --- | --- | --- | --- | --- | --- | --- | --- | --- |
| Solvent | Type | A-1 | A-2 | A-3 | A-4 | A-5 | A-6 | B-1 | B-2 | B-3 |
|  | Boiling point [° C.] | 111.2 | 140 | 51.1 | 172 | 45.3 | 96.5 | 61 | 76 | 98 |
|  | Extraction/removal index (r) | 3.3 | 4.6 | 6.1 | 3.9 | 2.2 | 1.3 | 9.8 | 9.6 | 9.5 |
|  | Amount used [g] | 155.5 | 142.2 | 50.0 | 180.5 | 186.4 | 228.2 | 290.2 | 280.7 | 317.1 |
| Gas flow rate [mL/min] |  | 12.9 | 14.6 | 14.4 | 15.5 | 17.1 | 15.4 | 14.9 | 16.1 | 16.4 |
| Gas flow amount [g] |  | 9.9 | 11.1 | 12.1 | 8.3 | 9.2 | 11.7 | 11.4 | 13.5 | 12.5 |
| Mixed gas | R-1234yf [vol %] | 96.46 | 88.32 | 81.27 | 86.69 | 85.72 | 79.94 | 85.97 | 97.33 | 91.85 |
|  | R-1243zf [vol %] | 0.51 | 0.32 | 0.94 | 0.74 | 0.99 | 5.35 | 0.32 | 0.50 | 0.31 |
|  | R-254eb [vol %] | 1.97 | 8.91 | 14.06 | 10.21 | 10.81 | 11.89 | 10.73 | 1.46 | 6.25 |
|  | R-1225ye [vol %] | 21.5 | 66.0 | 92.2 | 98.7 | 83.7 | 103.1 | 62.3 | 0.0 | 53.5 |
|  | R-1252zf [vol %] | 29.0 | 43.7 | 63.7 | 59.9 | 58.9 | 59.9 | 45.7 | 27.0 | 42.0 |
|  | R-263fb [vol %] | 0.07 | 0.17 | 0.26 | 0.25 | 0.24 | 0.25 | 0.19 | 0.06 | 0.14 |
|  | R-124 [vol %] | 0.20 | 0.56 | 0.87 | 0.77 | 0.77 | 0.80 | 0.63 | 0.17 | 0.45 |
| Purified gas | R-1234yf [vol %] | 98.66 | 97.75 | 94.44 | 96.45 | 96.12 | 93.07 | 95.46 | 98.52 | 95.21 |
|  | R-1243zf [vol %] | 0.30 | 0.21 | 0.78 | 0.49 | 0.68 | 3.48 | 0.33 | 0.50 | 0.35 |
|  | R-254eb [vol %] | 0.22 | 1.76 | 3.87 | 2.74 | 2.49 | 2.89 | 3.37 | 0.72 | 2.92 |
|  | R-1225ye [vol %] | 10.2 | 20.3 | 72.1 | 57.5 | 80.9 | 73.3 | 32.0 | 0.0 | 71.9 |
|  | R-1252zf [vol %] | 18.5 | 27.9 | 37.6 | 23.4 | 51.7 | 35.7 | 38.3 | 0.0 | 49.7 |
|  | R-263fb [vol %] | 0.01 | 0.06 | 0.14 | 0.10 | 0.09 | 0.09 | 0.11 | 0.04 | 0.13 |
|  | R-124 [vol %] | 0.03 | 0.11 | 0.40 | 0.09 | 0.23 | 0.24 | 0.30 | 0.10 | 0.27 |
| Removal rate [%] | R-1243zf | 41 | 34 | 17 | 33 | 32 | 35 | −4 | 0 | −14 |
|  | R-254eb | 89 | 80 | 72 | 73 | 77 | 76 | 69 | 51 | 53 |
|  | R-1225ye | 53 | 69 | 22 | 42 | 3 | 29 | 49 | — | −35 |
|  | R-1252zf | 36 | 36 | 41 | 61 | 12 | 40 | 16 | 100 | −18 |

TABLE 3-continued

|  | Ex. 1 | Ex. 2 | Ex. 3 | Ex. 4 | Ex. 5 | Ex. 6 | Ex. 7 | Ex. 8 | Ex. 9 |
|---|---|---|---|---|---|---|---|---|---|
| R-263fb | 80 | 66 | 46 | 59 | 63 | 63 | 40 | 30 | 10 |
| R-124 | 86 | 80 | 54 | 88 | 71 | 70 | 52 | 40 | 40 |

Abbreviations in Table 3 have the following meanings.
A-1: 2-chloro-2-methylpropane (HSP [15.6, 7.6, 2.0], extraction/removal index (r) = 3.3)
A-2: xylene (HSP [18.4, 4.4, 3.1], extraction/removal index (r) = 4.6)
A-3: $(CF_3)_2CHOCH_3$ (HSP [14.6, 5.1, 3.0], extraction/removal index (r) = 6.1)
A-4: cineol (HSP [16.7, 6.2, 2.8], extraction/removal index (r) = 3.9)
A-5: 3-chloro-1-propene (HSP [17.0, 6.2, 2.3], extraction/removal index (r) = 2.2)
A-6: 1,2-dichloropropane (HSP [17.3, 7.1, 2.9], extraction/removal index (r) = 1.3)
B-1: HFE-7100 (manufactured by 3M, HSP [13.5, 1.9, 1.5], extraction/removal index (r) = 9.8)
B-2: HFE-7200 (manufactured by 3M, HSP [13.7, 1.8, 1.5], extraction/removal index (r) = 9.6)
B-3: HFE-7300 (manufactured by 3M, HSP [14.2, 1.1, 0.8], extraction/removal index (r) = 9.5)
R-1234yf: 2,3,3,3-tetrafluoropropene
R-1243zf: 3,3,3-trifluoropropene
R-1225ye: 1,2,3,3,3-pentafluoropropene
R-1252zf: 3,3-difluoropropene
R-254eb: 1,1,1,2-tetrafluoropropane
R-263fb: 1,1,1-trifluoropropane
R-124: 1-chloro-1,2,2,2-tetrafluoroethane Method (β)

Example 10

Into a 50 mL autoclave made of SUS, 21.0 g of 2-chloro-2-methylpropane (extraction/removal index (r)=3.3) was charged as a solvent (A), and into the autoclave, 6.0 g of a mixed liquid obtained by liquefying a mixed gas and having a composition as shown in Table 4 containing R-1234yf as the main component, was added. After mixing at 20° C. for 2 hours, the pressure in the autoclave became 0.15 MPa(G). After the purification, a purified gas was recovered from the gas phase. The composition of the obtained purified gas and the removal rate X of each impurity are shown in Table 4.

Examples 11 to 18

A purified gas was recovered in the same manner as in Example 10 except that the type and amount of the solvent used, and the composition and amount of the mixed liquid used, were changed as shown in Table 4. The composition of the obtained purified gas and the removal rate of each impurity are shown in Table 4.

Further, the removal rate X of R-1243zf to the extraction/removal index (r) of a solvent in each of Examples 1 to 18 is shown in FIG. 1.

TABLE 4

|  |  | Ex. 10 | Ex. 11 | Ex. 12 | Ex. 13 | Ex. 14 | Ex. 15 | Ex. 16 | Ex. 17 | Ex. 18 |
|---|---|---|---|---|---|---|---|---|---|---|
| Solvent | Type | A-1 | A-2 | A-3 | A-4 | A-5 | A-6 | B-1 | B-2 | B-3 |
|  | Boiling point [° C.] | 111.2 | 140 | 51.1 | 172 | 45.3 | 96.5 | 61 | 76 | 98 |
|  | Extraction/removal index (r) | 3.3 | 4.6 | 6.1 | 3.9 | 2.2 | 1.3 | 9.8 | 9.6 | 9.5 |
|  | Amount used [g] | 21.0 | 21.6 | 34.4 | 23.1 | 23.1 | 28.7 | 38.1 | 35.8 | 41.6 |
| Amount of mixed liquid used [g] |  | 6.0 | 5.6 | 6.0 | 6.5 | 5.7 | 5.6 | 6.0 | 6.0 | 5.9 |
| Pressure [MPa(G)] |  | 0.09 | 0.13 | 0.04 | 0.18 | 0.12 | 0.15 | 0.08 | 0.06 | 0.08 |
| Mixed liquid | R-1234yf [vol %] | 87.61 | 87.47 | 83.65 | 84.76 | 84.61 | 81.16 | 85.57 | 85.57 | 86.83 |
|  | R-1243zf [vol %] | 0.79 | 0.83 | 0.82 | 0.69 | 0.97 | 5.22 | 0.80 | 0.81 | 0.79 |
|  | R-254eb [vol %] | 9.36 | 10.97 | 12.50 | 11.79 | 11.66 | 11.08 | 10.86 | 10.99 | 10.06 |
|  | R-1225ye [vol %] | 83.7 | 79.9 | 91.1 | 94.0 | 86.3 | 99.8 | 69.8 | 75.4 | 80.4 |
|  | R-1252zf [vol %] | 51.5 | 52.9 | 58.0 | 59.7 | 60.2 | 57.8 | 55.0 | 53.8 | 50.4 |
|  | R-263fb [vol %] | 0.21 | 0.22 | 0.24 | 0.25 | 0.25 | 0.24 | 0.20 | 0.22 | 0.21 |
|  | R-124 [vol %] | 0.69 | 0.71 | 0.77 | 0.80 | 0.80 | 0.77 | 0.63 | 0.71 | 0.65 |
| Purified gas | R-1234yf [vol %] | 94.34 | 94.18 | 92.58 | 93.30 | 93.78 | 90.85 | 93.50 | 92.45 | 92.56 |
|  | R-1243zf [vol %] | 0.61 | 0.59 | 0.77 | 0.56 | 0.71 | 3.83 | 0.80 | 0.81 | 0.82 |
|  | R-254eb [vol %] | 3.84 | 4.40 | 5.27 | 5.46 | 4.25 | 4.45 | 4.64 | 5.56 | 5.43 |
|  | R-1225ye [vol %] | 69.1 | 0.0 | 75.0 | 71.6 | 87.4 | 91.7 | 67.0 | 71.4 | 68.8 |
|  | R-1252zf [vol %] | 36.5 | 34.7 | 42.0 | 33.3 | 43.7 | 45.3 | 33.8 | 40.1 | 38.2 |
|  | R-263fb [vol %] | 0.15 | 0.11 | 0.16 | 0.15 | 0.12 | 0.12 | 0.11 | 0.16 | 0.16 |
|  | R-124 [vol %] | 0.41 | 0.24 | 0.47 | 0.18 | 0.33 | 0.34 | 0.27 | 0.45 | 0.44 |
| Removal rate [%] | R-1243zf | 24 | 29 | 7 | 18 | 27 | 27 | 0 | 1 | −5 |
|  | R-254eb | 59 | 60 | 58 | 54 | 64 | 60 | 57 | 49 | 46 |
|  | R-1225ye | 17 | 100 | 18 | 24 | −1 | 8 | 4 | 5 | 14 |
|  | R-1252zf | 29 | 34 | 28 | 44 | 28 | 22 | 39 | 26 | 24 |
|  | R-263fb | 31 | 50 | 32 | 38 | 50 | 49 | 46 | 28 | 21 |
|  | R-124 | 41 | 67 | 38 | 78 | 58 | 56 | 57 | 37 | 33 |

Here, the abbreviations in Table 4 have the same meanings as in Table 3.

As shown in Table 3 and FIG. 1, in Examples 1 to 6 wherein according to the method (α), a mixed gas was brought into contact with a solvent (A) having an extraction/removal index (r) of at most 6.5, even R-1243zf close to R-1234yf particularly in the boiling point, was removed at a high efficiency, as compared with Examples 7 to 9 wherein a solvent having an extraction/removal index (r) exceeding 6.5, was used. Likewise, as shown in Table 4 and FIG. 1, in Examples 10 to 15 wherein according to the method (β) a mixed liquid was brought into contact with a solvent (A) having an extraction/removal index (r) of at most 6.5, even R-1243zf close to R-1234yf particularly in the boiling point, was removed at a high efficiency, as compared with Examples 16 to 18 wherein a solvent having an extraction/removal index (r) exceeding 6.5, was used.

INDUSTRIAL APPLICABILITY

According to the purification method of the present invention, it is possible to remove even impurities such as R-1243zf, etc. which are close to R-1234yf in their boiling points, and thus, the method is useful for e.g. purification of a product obtained by hydrogen reduction of R-1214ya.

This application is a continuation of PCT Application No. PCT/JP2012/052545, filed on Feb. 3, 2012, which is based upon and claims the benefit of priority from Japanese Patent Application No. 2011-022871 filed on Feb. 4, 2011. The contents of those applications are incorporated herein by reference in its entirety.

What is claimed is:

1. A method for purifying 2,3,3,3-tetrafluoropropene, the method comprising
bringing a mixture, which comprises 2,3,3,3-tetrafluoropropene as the main component and also comprises hydrohaloalkene impurities and hydrohaloalkane impurities, into contact with a solvent that has an extraction/removal index (r), as represented by formula (1), of at most 6.5, so as to remove at least a part of the hydrohaloalkene impurities and at least a part of the hydrohaloalkane impurities:

$$r=[4\times(\delta D-17.2)^2+(\delta P-8.3)^2+(\delta H-2.6)^2]^{1/2} \quad (1)$$

wherein $\delta D$, $\delta P$ and $\delta H$ are Hansen solubility parameters of the solvent, which are, respectively, dispersion parameter, polar parameter and hydrogen bonding parameter of the solvent, the unit of each of which is $(MPa)^{1/2}$.

2. The method according to claim 1, wherein the hydrohaloalkene impurities comprise a hydrohalopropene.

3. The method according to claim 1, wherein the hydrohaloalkane impurities comprise at least one of a hydrohalopropane and a hydrohaloethane.

4. The method according to claim 1, wherein at least a part of at least one member selected from the group consisting of 3,3,3-trifluoropropene, 3,3-difluoropropene and 1,2,3,3,3-pentafluoropropene, as the hydrohaloalkene impurities, is removed from the mixture.

5. The method according to claim 1, wherein at least a part of 3,3,3-trifluoropropene, as the hydrohaloalkene impurities, is removed from the mixture.

6. The method according to claim 1, wherein at least a part of at least one member selected from the group consisting of 1,1,1,2-tetrafluoropropane, 1,1,1-trifluoropropane and 1-chloro-2,2,2-tetrafluoroethane, as the hydrohaloalkane impurities, is removed from the mixture.

7. The method according to claim 1, wherein the mixture to be brought into contact with the solvent, is gaseous.

8. The method according to claim 1, wherein the solvent is at least one selected from the group consisting of anisole, 4-bromo-1-butene, 2-bromobutane, butyl propionate, butyl mercaptan, 3-chloro-1-propene, 2-chloro-2-methylpropane, 1-chlorobutane, decyl aldehyde, dibutyl sebacate, dibutyl sulfide, 1,1-dichloroethane, 1,2-dichloropropane, diethyl ketone, diethylene glycol dibutyl ether, diethylene glycol dimethyl ether, diisodecyl phthalate, 3-heptanone, hexyl formate, isophorone, methyltrichlorosilane, 2-methyltetrahydrofuran, paraldehyde, tetrahydrofuran, 1,1,1-trichloroethane, 2,3-butanedione, 2-chloroethyl ethyl ether, 1,8-cineole, chlorocyclohexane, 1,1-dichloroacetone, dihydropyran, 1,3-dimethoxybutane, ethylene glycol butylmethyl ether, ethylene glycol dibutyl ether, menthofuran, menthyl acetate, 2-methoxytetrahydropyran, 3-methylcyclohexanone, 2-methyl-1,3-dioxolane, tetrahydropyran, trichloroacetonitrile, ethyl phenyl acetate, 4-methoxytoluene, ethylal, carvone, γ-dodecalactone, isobornyl acetate, methoxycyclopentane, and xylene.

9. The method according to claim 1, wherein the solvent is at least one selected from the group consisting of anisole, 2-bromobutane, butyl propionate, 2-chloro-2-methylpropane, 1,1-dichloroethane, 1,2-dichloropropane, diethyl ketone, diethylene glycol dimethyl ether, hexyl formate, isophorone, paraldehyde, tetrahydrofuran, 2,3-butanedione, 1,1-dichloroacetone, menthofuran, 2-methoxytetrahydropyran, 3-methylcyclohexanone, 2-methyl-1,3-dioxolane, tetrahydropyran, trichloroacetonitrile, ethyl phenyl acetate, 4-methoxytoluene, ethylal, carvone, γ-dodecalactone, isobornyl acetate, and xylene.

10. The method according to claim 1, wherein the solvent is at least one selected from the group consisting of 2-bromobutane, 2-chloro-2-methylpropane, 1,1-dichloroethane, 1,2-dichloropropane, diethyl ketone, 1,1-dichloroacetone, 3-methylcyclohexanone, trichloroacetonitrile, γ-dodecalactone, and xylene.

* * * * *